United States Patent [19]

Kishimoto et al.

[11] Patent Number: 5,206,201

[45] Date of Patent: Apr. 27, 1993

[54] CATALYST FOR PRODUCTION OF SUBSTITUTED BENZALDEHYDE AND METHOD FOR PRODUCTION OF THE CATALYST

[75] Inventors: Nobuji Kishimoto; Isao Nakamura, both of Osaka; Taizou Matsueda, Amagasaki; Yoshitaka Arita, Kobe, all of Japan

[73] Assignee: Nippon Shokubai Co., Ltd., Osaka, Japan

[21] Appl. No.: 704,069

[22] Filed: May 22, 1991

[30] Foreign Application Priority Data

May 25, 1990 [JP] Japan .................................. 2-134105
May 25, 1990 [JP] Japan .................................. 2-134106

[51] Int. Cl.$^5$ .......................... B01J 21/02; B01J 23/02; B01J 23/22; B01J 23/28
[52] U.S. Cl. .................................... 502/206; 502/209; 502/215; 502/312
[58] Field of Search ................ 502/206, 209, 312, 215; 568/431

[56] References Cited

U.S. PATENT DOCUMENTS

| | | | |
|---|---|---|---|
| 3,857,796 | 12/1974 | Takenaka et al. | 502/312 |
| 4,070,379 | 1/1978 | Ciquier et al. | 260/346.75 |
| 4,118,402 | 10/1978 | Suzuki et al. | 260/346.75 |
| 4,700,009 | 10/1987 | Nosberger | 568/431 |

FOREIGN PATENT DOCUMENTS

| | | |
|---|---|---|
| 0009239 | 2/1980 | European Pat. Off. . |
| 0196601 | 8/1986 | European Pat. Off. . |
| 0265733 | 5/1988 | European Pat. Off. . |
| 2112938 | 1/1972 | Fed. Rep. of Germany ...... 502/312 |

*Primary Examiner*—W. J. Shine
*Attorney, Agent, or Firm*—Omri M. Behr; Matthew J. McDonald

[57] ABSTRACT

A catalyst for the production of a substituted benzaldehyde by catalytic vapor-phase oxidation of a substituted toluene, which catalyst has as a catalytically active substance being composed of an oxide represented by the general formula III:

$$V_a Mo_b X_c Y_d O_e \qquad (III)$$

wherein V, Mo, and O are respectively for vanadium, molybdenum, and oxygen, X is at least one element selected from the group consisting of sodium, potassium, rubidium, cesium, and thallium, Y is at least one element selected from the group consisting of niobium, tantalum, phosphorus, antimony, bismuth, tellurium, tin, lead, boron, copper, and silver, and a, b, c, d, and e indicate the atomic ratios of relevant elements such that where a+b=1, then b=0.05 to 0.4, c=0.1 to 1, d=0 to 1, and e=the value determined by the state of oxidation of other elements.

10 Claims, No Drawings

CATALYST FOR PRODUCTION OF SUBSTITUTED BENZALDEHYDE AND METHOD FOR PRODUCTION OF THE CATALYST

BACKGROUND OF THE INVENTION

1. Field of the Invention

This invention relates to a catalyst for the production of a substituted benzaldehyde, a method for the production of the catalyst, and a method for the production of a substituted benzaldehyde. More particularly, it relates to a catalyst for the production of a substituted benzaldehyde by catalytic vapor-phase oxidation of a corresponding substituted toluene with a molecular oxygen-containing gas and consequent selective oxidation of the methyl group of the substituted toluene, a method for the production of the catalyst, and a method for the production of the substituted benzaldehyde.

2. Description of the Prior Art

The substituted benzaldehydes are highly useful intermediates for the production of medicines, agricultural pesticides, and perfumes in the organic chemical industry.

As methods for the production of such substituted benzaldehydes as tert-butyl benzaldehyde and methoxy benzaldehyde, liquid-phase oxidation and electrolytic oxidation have been known to the art (as disclosed in JP-A-52-125,137(1977), JP-A-54-109,937(1979), JP-A-55-85,682(1980), and JP-A-56-127,327(1981), for example). These methods, however, do not deserve to be called as economically advantageous measures because they require an extra step of treatment for disposal of water in order form them to be carried out on a commercial scale, necessitate an unduly high power cost, and entail a complicate process. For the solution of these problems, a desire is expressed for a method which attains the production of a substituted benzaldehyde by economically advantageous vapor-phase oxidation.

As respects the production of tert-butylbenzaldehyde by catalytic vapor-phase oxidation of corresponding tert-butyltoluene, a method which uses a molybdenum-bismuth-iron-nickel type catalyst (DE-A. 2,841,712) and a method which uses a molybdenum-copper-tin type catalyst (U.S. Pat. No. 4,700,009) have been known to the art. These catalysts are both extremely deficient in activity and selectivity.

A method which uses a vanadium-alkali metal type catalyst has been also known to the art (JP-B.2-9,014(1990)). Though the catalyst used in this method exhibits fairly high activity and selectivity, it cannot be safely called fully satisfactory for commercialization of this method.

As respects the production of methoxybenzaldehyde by catalytic vapor-phase oxidation of corresponding methoxy toluene, a method which uses a vanadium-alkali metal type catalyst (JP-B.63-12,857(1988) and JP-B-63-12,858(1988)), a method which uses a vanadium-thallium type catalyst (JP-B.-63-47,697(1988)), and a method which uses a vanadium-silver type catalyst (JP-A.2-53,750(1990)) have been known to the art. Though these catalysts exhibit fairly high activity and selectivity, their qualities have room for more improvement.

The production of other substituted benzaldehydes by catalytic vapor-phase oxidation is still inferior in technical level to the production of tert-butylbenzaldehyde and methoxybenzaldehyde.

The conventional catalysts disclosed for use in the production of substituted benzaldehydes by selective catalytic vapor-phase oxidation of the methyl group of corresponding substituted toluenes having tert-butyl group, methoxy group, phenoxy group, isopropyl group, and hydroxyl group as a substituent cannot be safely said to possess fully satisfactory quality suitable for actual use.

One object of this invention, therefore, is to provide a catalyst suitable for the production of substituted benzaldehydes by catalytic vapor-phase oxidation of corresponding substituted toluenes having tert-butyl group, methoxy group, phenoxy group, isopropyl group, and hydroxyl group as a substituent.

Another object of this invention is to provide a method for the production of the aforementioned catalyst for use in the production of the substituted benzaldehydes.

Yet another object of this invention is to provide a method for producing a substituted benzaldehyde in a high yield with high selectivity by catalytic vapor-phase oxidation of a corresponding substituted toluene having tert-butyl group, methoxy group, phenoxy group, isopropyl group, and a hydroxyl group as a substituent.

SUMMARY OF THE INVENTION

These objects are accomplished by a catalyst for the production of a substituted benzaldehyde represented by the general formula I:

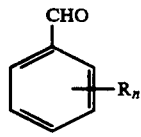

(I)

wherein R is tert-butyl group, methoxy group, phenoxy group, isopropyl group or hydroxyl group and n is an integer in the range of from 1 to 3, by catalytic vapor-phase oxidation of a corresponding substituted toluene represented by the general formula II:

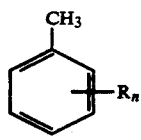

(II)

wherein R and n are the same meanings as defined above, which catalyst has as a catalytically active substance being composed of an oxide represented by the general formula III

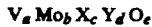

$$V_a Mo_b X_c Y_d O_e \quad (III)$$

wherein V, Mo, and O are respectively vanadium, molybdenum, and oxygen, X is at least one element selected from the group consisting of sodium, potassium, rubidium, cesium, and thallium, Y is at least one element selected from the group consisting of niobium, tantalum, phosphorus, antimony, bismuth, tellurium, tin, lead, boron, copper, and silver, and a, b, c, d, and e are atomic ratios of the relevant elements such that where $a+b=1$, then $b=0.05$ to 0.4, $c=0.1$ to 1, $d=0$ to 1, and e=the value to be fixed by the state of oxidation of the other elements.

The objects are further accomplished by a method for the production of a catalyst to be used in the production of a substituted benzaldehyde by catalytic vapor-phase oxidation of a corresponding substituted toluene, which method comprises mixing starting raw materials for the catalytically active substance formed of an oxide represented by the general formula III with powdered inactive carrier and then drying and calcining the resultant composite, and a catalyst obtained by this method.

The objects are further accomplished by a method for the production of a catalyst to be used in the production a substituted benzaldehyde by catalytic vapor-phase oxidation of a corresponding substituted toluene, which method comprises depositing on an porous inactive carrier starting raw materials for a catalytically active substance formed of an oxide represented by the general formula III and then drying and calcining the resultant composite, and a catalyst obtained by this method.

The objects are also accomplished by a method for the production of a substituted benzaldehyde represented by the general formula I, which method comprises subjecting a corresponding substituted toluene represented by the general formula II to catalytic vapor-phase oxidation with a molecular oxygen-containing gas in the presence of a catalyst having a catalytically active substance being composed of an oxide represented by the general formula III.

The catalyst to be used in the method of the present invention contains molybdenum as an essential component besides vanadium. This catalyst exhibits appreciably improved selectivity as compared with a comparable catalyst containing no molybdenum. This fact seems to imply that molybdenum contributes to the improvement of selectivity.

It is believed that the component element X represses the activity of combustion and contributes to the improvement of selectivity, though it adversely affects the overall activity and that the component element Y contributes to the improvement of activity or selectivity.

During the preparation of the catalyst of this invention, the addition of an oxyacid to the impregnating solution enables uniformization of the impregnating solution to be attained effectively. The produced catalyst, therefore, enjoys uniformity in composition of the catalytically active component thereof. As a result, the selectivity is improved, the selective oxidation of the methyl group aimed at is carried out effectively, and the substituted benzaldehyde aimed at is produced with high efficiency.

By carrying out catalytic vapor-phase reaction of this invention in the presence of the catalyst constructed as described above, a substituted benzaldehyde can be produced in a high yield with high selectivity from a corresponding substituted toluene. The method of this invention, therefore, is unusually advantageous for commercial production of such substituted benzaldehydes as tert-butylbenzaldehyde and methoxybenzaldehyde which are useful intermediates for medicines, agricultural pesticides, perfumes, etc.

EXPLANATION OF THE PREFERRED EMBODIMENT

The catalytically active substance to be used in the catalyst of this invention is a composite oxide represented by the general formula III:

$$V_a Mo_b X_c Y_d O_e \qquad (III)$$

wherein V, Mo, and O are respectively vanadium, molybdenum, and oxygen, X is at least one element selected from the group consisting of sodium, potassium, rubidium, cesium, and thallium, Y is at least one element selected from the group consisting of niobium, tantalum, phosphorus, antimony, bismuth, tellurium, tin, lead, boron, copper, and silver, a, b, c, d, and e are the atomic ratios of the relevant elements such that where $a+b=1$ is satisfied, then $b=0.05$ to 0.4, preferably 0.1 to 0.3, $c=0.1$ to 1, preferably 0.1 to 0.7, $d=0$ to 1, preferably 0 to 0.5, and e=the value to be determined by the state of oxidation of the other elements.

As a method for preparing the catalytically active substance on the catalyst, the following methods can be cited, but the present invention is not limited by the method.

The starting raw materials to be used for the preparation of the catalytically active substance are not particularly limited. Various known starting raw materials are usable. The vanadium sources which are effectively usable herein include ammonium metavanadate, vanadium pentoxide, vanadyl oxalate, and vanadyl sulfate, for example. The molybdenum sources which are effectively usable herein include ammonium paramolybdate, molybdic acid, and molybdenum oxide, for example. The X component element sources which are advantageously usable herein include nitrates, carbonates, and sulfates of the indicated elements, for example The Y component element sources which are effectively usable herein include such phosphorus sources as phosphoric acid and ammonium phosphate, such antimony sources as antimony trioxide and antimony pentoxide, such boron sources as boric acid, and other element sources in the form of suitable compounds, for example.

As the catalyst for use in this invention, the catalytically active substance mentioned above may be exclusively molded in a prescribed shape and the resultant molded mass put to use in its unmodified form. Optionally, this catalytically active substance may incorporate therein a powdered inactive carrier such as, for example, diatomaceous earth, silica, alumina, silicon carbide, zirconia, or titania before it is molded into the shape of spheres, circular cylinders, rings, or fragments. When the catalyst uses a powdered inactive carrier, the amount of the carrier to be used is not particularly limited. Generally, however, this amount is preferable to be in the range of from 10 to 80% by weight based on the amount of the catalyst in its finished form.

The method to be employed for the preparation of the catalyst for use in this invention is not particularly limited. This catalyst can be prepared by any of the methods generally employed for the preparation of catalysts of this class. The production of the catalyst by a typical method is effected by first preparing an aqueous solution containing a vanadium source compound and a molybdenum source compound, mixing this aqueous solution with an X component element source compound and a Y component element source compound, kneading the mixture thoroughly with a powdered inactive carrier added thereto in an amount calculated to account for a proportion in the range of from 10 to 80% by weight based on the amount of the finally produced catalyst in its finished form, concentrating the resultant blend under a vacuum, molding the concentrated blend in a prescribed shape, drying the molded mass at a temperature in the range of from 80° to 300° C., preferably from 90° to 250° C., and further calcining the dried molded mass in the air at a temperature in the range of from 450° to 900° C., preferably from 500° to 800° C. Alternatively, the aforementioned blend may be dried and calcined under the same conditions as described above.

As alternative method for production of the catalyst to be used in the present invention, there is a method by depositing the starting raw materials for the catalytically active substance on a porous inactive carrier, drying the deposited carrier and calcining it. That is, as the porous inactive carrier, there are silicon carbide, alumina, silica, silica-alumina and like the carriers which are generally used in the art. The catalytically active substance is deposited by impregnating and dipping the carrier into an aqueous solution or slurry of the substance, drying the impregnated carrier and calcining it. Alternatively, the catalytically active substance can be deposited by spraying an aqueous solution or slurry of the starting raw material on a heated carrier and baking it on the carrier.

In the catalyst of this invention, when the catalytically active substance is to be deposited on the porous inactive carrier mentioned above, the amount of the catalytically active substance to be deposited is in the range of from 3 to 20% by weight, preferably from 5 to 15% by weight, based on the weight of the porous carrier. If the amount of the catalytically active substance to be deposited is less than 3% by weight, the produced catalyst betrays deficiency in activity and fails to exhibit the desired catalytic activity. Conversely, if this amount exceeds 20% by weight, the excess is wasted without bringing about a proportionate increase in the catalytic activity.

The porous inactive carrier to be used in this invention may be in the shape of spheres, circular cylinders, rings, or fragments, for example.

As the porous inactive carrier used for depositing the catalytically active substance, although various carrier used in the art may be used, porous inactive carrier having silicon carbide content of not less than 80% by weight, preferably 95% by weight, an apparent porosity in the range of 20 to 60%, preferably 30 to 50%, and a specific surface area in the range of 0.01 to 1 $m^2/g$, preferably 0.05 to 0.5 $m^2/g$ is especially preferable. If the apparent porosity is less than 20%, the deposition of the catalytically active substance for acquiring necessary activity is attained only with difficulty and the produced catalyst suffers from inferior quality. Conversely, if the apparent porosity exceeds 60%, the produced catalyst betrays deficiency in strength and in practicability as well. If this specific surface area is less than 0.01 $m^2/g$, the produced catalyst is notably deficient in activity. Conversely, if this specific surface area exceeds 1 $m^2/g$, the produced catalyst is conspicuously deficient in selectivity.

The apparent porosity as used in this invention has been determined in accordance with the procedure of JIS R 2205 with necessary modifications and the specific surface area has been determined in accordance with the Brunauer-Emmett-Teller (BET) method ($N_2$ adsorption or Kr adsorption).

If the catalyst of this invention for the production of a substituted benzaldehyde uses as its carrier a porous inactive carrier of silicon carbide possessing the above-mentioned specific physical properties, it exhibits conspicuously improved selectivity as compared with the catalyst using other carrier.

As one cause for the improved selectivity, the high thermal conductivity of silicon carbide may be cited. Generally, the reaction of oxidation which occurs on the catalyst generates a large volume of heat. This heat ordinarily brings about an elevation of the temperature of the catalyst bed and possibly gives rise to an abnormally hot part called a hot spot locally in the catalyst. Owing to the loss through consecutive oxidation of the partial oxidation product aimed at, this hot spot in most cases results in a decline of the selectivity. When the porous inactive carrier of silicon carbide possessing high thermal conductivity is used, it allows effective removal of this heat, minimizes the elevation of the temperature of the catalyst bed, precludes the occurrence of the hot spot, and enables the selectivity to be improved. Further, the fact that the silicon carbide itself is inactive to the chemical reaction at which this invention is aimed also constitutes itself one important factor.

As an embodiment of the method for production of the catalyst in accordance with the present invention, the following method can be cited. To be specific, the impregnating solution is obtained by weighing the starting raw materials for vanadium, molybdenum, an X component source, and a Y component source in respective amounts calculated to account for prescribed molar ratios, converting them by addition of water into an aqueous solution or slurry, and if necessary, adding an oxyacid to the aqueous solution or slurry. When the oxyacid is used, the order in which the starting raw materials and the oxyacid are to be added is not particularly limited. For example, the impregnating solution may be obtained by adding the starting raw materials to an aqueous oxyacid solution, by sequentially adding and admixing the starting raw materials and adding the oxyacid during the course of the sequential addition of the raw materials, or by mixing the starting raw materials and, after completion of the mixing, adding the oxyacid to the resultant mixture.

In accordance with the method of this invention for the production of the catalyst, it is preferable that the deposition of the catalytically active substance on the porous inactive carrier starts from the preparation of an impregnating solution containing the starting raw materials for the components of a dried catalytically active substance and an oxyacid.

The incorporation of the oxyacid serves the purpose of improving the catalyst quality as evinced by the enhancement in selectivity. Though the reason for this improvement is not fully clear, this improvement may be logically explained by a postulate that the added oxyacid uniformizes the impregnating solution and represses the otherwise possible loss (impairment) of the uniformity of the composition of the catalytically active substance during the deposition of this substance on the carrier. The oxyacid to be used herein is not limited to any specific kind. The oxyacids which are usable particularly advantageously herein are lactic acid, malic acid, tartaric acid, and citric acid, for example. These oxyacids may be used either singly or in the form of a mixture of two or more members.

The amount of the oxyacid to be used is preferable to be not less than equimolar to vanadium, preferably to be in the range of from 1 to 2 mols per mol of vanadium. If the amount of the oxyacid to be used is unduly small, the impregnating solution possibly loses its uniformity of composition and the produced catalyst suffers from deficiency in quality. Conversely, if this amount is unduly large, the excess is wasted without promoting its effect. Then, the impregnating solution obtained as described above is deposited on a porous carrier. The method to be employed for this deposition of the impregnating solution is not particularly limited. Generally, the method which resides in immersing the porous carrier in the impregnating solution is advantageously employed.

The amount of the catalytically active substance to be deposited is adjusted, as already mentioned, in the range of from 3 to 20% by weight, preferably from 5 to 15% by weight, based on the weight of the carrier. This adjustment of the amount of deposition can be easily effected by suitably varying the concentration of the impregnating solution or the number of cycles of depositing treatment (repeated deposition).

After the deposition of the impregnating solution is completed, the catalyst aimed at is obtained by drying and subsequently calcining the solution as deposited on the carrier.

The conditions for the drying are not particularly limited. The drying is carried out advantageously under a reduced pressure or in a draft. Generally, the drying temperature used in this case is in the range of from 80° to 300°, preferably from 90° to 250° C.

The conditions for the calcination are not particularly limited. Generally, the calcination is carried out at a temperature in the range of from 450° to 900° C., preferably from 500° to 800° C. When the amount of the catalytically active substance to be deposited is adjusted by the adjustment of the repeated deposition mentioned above, this adjustment may be effected by suitably repeating the procedure of deposition - drying - deposition or deposition - drying - calcination - deposition.

The substituted toluenes represented by the aforementioned general formula (II) and used effectively for the method of this invention include p-tert-butyltoluene, 2,4-di-tert-butyltoluene, p-methoxytoluene, 3,4-dimethoxytoluene, 3,4,5-trimethoxytoluene, p-phenoxytoluene, m-phenoxytoluene, o-isopropyltoluene, m-isopropyltoluene, p-isopropyltoluene, 2,4-diisopropyltoluene, o-hydroxytoluene, and p-hydroxy-toluene, for example. Optionally, two or more such substituted toluenes may be used in a combined state.

In accordance with the method of this invention, by catalytic vapor-phase oxidation of the aforementioned substituted toluene, the methyl group is selectively oxidized and the substituted benzaldehyde is obtained. To be specific, p-tert-butylbenzaldehyde is obtained from p-tert-butyltoluene, p-methoxybenzaldehyde from p-methoxytoluene, p-phenoxybenzaldehyde from p-phenoxytoluene, p-isopropylbenzaldehyde from p-isopropyltoluene, and p-hydroxybenzaldehyde from p-hydroxytoluene, for example.

The catalytic vapor-phase oxidation of the present invention can be carried out advantageously by supplying a feed gas containing 0.1 to 2% by volume of a given substituted toluene as the raw material and 98 to 99.9% by volume of air at a space velocity in the range of from 500 to 10,000 hr$^{-1}$ (STP basis) at a reaction temperature in the range of from 300° to 600° C., preferably from 400° to 500° C, into contact with the catalyst described above. In this case, part of the air mentioned above may be substituted with such an inert gas as nitrogen. Optionally, the air may be partly substituted with oxygen within the limits in which the possibility of explosion is absent, so that the reaction proceeds in an atmosphere rich in oxygen. Although catalytic vapor-phase oxidation is generally carried out under normal pressure, it may be performed under reduced pressure or under increased pressure. The mode of the reaction is not particularly limited. Though the reaction may be carried out in the fixed bed mode, the fluidized bed mode, or the moving bed mode, it is generally preferable to be performed in the fixed bed mode. Further, the reaction may be in the single-pass pattern or the recycle pattern.

Now, the present invention will be described more specifically below with reference to working examples.

The conversion, the per-pass yield, and the selectivity are defined by the following formulas.

Conversion (mol %)=(Number of mols of reacted substituted toluene)/(number of mols of supplied substituted toluene)×100

Per-pass yield (mol %)=(Number of mols of formed substituted benzaldehyde)/(number of mols of supplied substituted toluene)×100

Selectivity (mol %)=(Number of mols of formed substituted benzaldehyde)/(number of mols of reacted substituted toluene)×100

EXAMPLE 1

A homogeneous solution was prepared by adding 9.36 g of ammonium metavanadate and 3.33 g of ammonium paramolybdate and further adding 14.0 g of oxalic acid to 200 ml of hot water. To this homogeneous solution, an aqueous solution of 5.85 g of cesium nitrate in 50 ml of water and an aqueous solution of 1.01 g of potassium nitrate in 10 ml of water were added. The resultant mixture was stirred at 70° C. for about one hour, then admixed with 6.82 g of diatomaceous earth (produced by Jones Mansvill Product Corp. and marketed under trademark designation of "Celite"), and concentrated by heating. The concentrate consequently obtained was dried at 120° C. for two hours and further at 220° C. for 16 hours and then calcined at 600° C. for six hours to produce a catalyst (A).

The composition of this catalyst (A) in atomic ratio exclusive of oxygen was as follows:

$$V_{0.8} Mo_{0.2} Cs_{0.3} K_{0.1}$$

This catalyst was pulverized to 9 to 20 mesh. A portion, 15 ml in volume, of the pulverized catalyst was placed in a U-shaped reaction tube of stainless steel having an inside diameter of 10 mm.

A feed gas containing of 0.9% by volume of p-tert-butyltoluene and 99.1% by volume of air was introduced into the reaction tube to effect reaction at a space velocity of 5,000 hr$^{-1}$ (STP) and a reaction temperature of 450° C. and obtain p-tert-butylbenzaldehyde. The results are shown in Table 1.

EXAMPLE 2

A catalyst (B) was prepared by following the procedure of Example 1, except that an aqueous solution of 0.62 g of boric acid (H$_3$BO$_3$) in 10 ml of water and 2.92 g of antimony trioxide were added in the place of potassium nitrate after the addition of cesium nitrate.

The composition of this catalyst (B) in atomic ratio exclusive of oxygen was as follows:

$$V_{0.8} Mo_{0.2} Cs_{0.3} Sb_{0.2} B_{0.1}$$

Thereafter, the catalyst (B) was subjected to the same reaction as in Example 1, except that the reaction temperature was changed to 435° C. The results are shown in Table 1.

EXAMPLE 3

A catalyst (C) was prepared by following the procedure of Example 1, except that 3.46 g of 85% phosphoric acid was added and an aqueous solution of 1.70 g of silver nitrate in 10 ml of water was further added after the addition of potassium nitrate. The composition of this catalyst (C) in atomic ratio exclusive of oxygen was as follows:

$$V_{0.8} Mo_{0.2} Cs_{0.3} K_{0.1} P_{0.3} Ag_{0.1}$$

Thereafter, the catalyst (C) was subjected to the same reaction as in Example 1, except that the reaction temperature was changed to 425° C. The results are shown in Table 1.

EXAMPLE 4

A homogeneous solution was prepared by adding 8.78 g of ammonium metavanadate and 4.42 g of ammonium paramolybdate and further adding 13.2 g of oxalic acid to 200 ml of hot water. To the homogeneous solution, aqueous solutions of 4.42 g of rubidium nitrate in 10 ml of water and 1.01 g of potassium nitrate in 10 ml of water and 4.83 g of copper (II) nitrate ($Cu(NO_3)_2 \cdot 3H_2O$) in 10 ml of water were added and 1.60 g of tellurium dioxide was further added. The mixture consequently obtained was stirred at 70° C. for about one hour, admixed with the same diatomaceous earth as used in Example 1, and then concentrated by heating. The resultant concentrate was dried first at 120° C. for two hours and then at 220° C. for 16 hours and subsequently calcined at 600° C. for six hours to obtain a catalyst (D).

The composition of this catalyst (D) in atomic ratio exclusive of oxygen was as follows:

$$V_{0.75} Mo_{0.25} Rb_{0.3} K_{0.1} Cu_{0.2} Te_{0.1}$$

Thereafter, the catalyst (D) was subjected to the same reaction as in Example 1, except that the reaction temperature was changed to 430° C. The results are shown in Table 1.

EXAMPLE 5

A homogeneous solution was prepared by adding 8.19 g of ammonium metavanadate and 5.31 g of ammonium paramolybdate and further adding 12.2 g of oxalic acid to 200 ml of hot water. To the homogeneous solution, 2.31 g of 85% phosphoric acid was added and aqueous solutions of 7.99 g of thallium (I) nitrate in 50 ml of water and 2.61 g of barium nitrate in 10 ml of water were further added. The mixture consequently obtained was stirred at 70° C. for about one hour, then admixed with 6.82 g of the same diatomaceous earth as used in Example 1, and concentrated by heating. The resultant concentrate was dried first at 120° C. for two hours and then at 220° C. for 16 hours and subsequently calcined at 600 C for six hours to obtain a catalyst (E).

The composition of this catalyst (E) in atomic ratio exclusive of oxygen was as follows:

$$V_{0.7} Mo_{0.3} Tl_{0.3} P_{0.2} Ba_{0.1}$$

Thereafter, the catalyst (E) was subjected to the same reaction as in Example 1, except that the reaction temperature was changed to 430° C. The results are shown in Table 1.

EXAMPLE 6

A homogeneous solution was prepared by adding 10.53 g of ammonium metavanadate and 1.77 g of ammonium paramolybdate and further adding 15.8 g of oxalic acid to 200 ml of hot water. To the homogeneous solution, aqueous solutions of 5.85 g of cesium nitrate in 50 ml of water, 3.40 g of silver nitrate in 10 ml of water, and 3.31 g of lead (II) nitrate ($Pb(NO_3)_2$) in 10 ml of water were added. The mixture consequently obtained was stirred at 70° C. for about one hour, then admixed with 6.82 g of the same diatomaceous earth as used in Example 1, and subsequently concentrated by heating. The resultant concentrate. The resultant concentrate was dried at 120° C. for two hours and at 220° C. for 16 hours and subsequently calcined at 600° C. for six hours to obtain a catalyst (F).

The composition of this catalyst (F) in atomic ratio exclusive of oxygen was as follows:

$$V_{0.9} Mo_{0.1} Cs_{0.3} Ag_{0.2} Pb_{0.1}$$

Subsequently, the catalyst (F) was subjected to the same reaction as in Example 1, except that the reaction temperature was changed to 425° C. The results are shown in Table 1.

Control 1

A catalyst (G) was prepared by following the procedure of Example 2, except that the amount of ammonium metavanadate to be used was changed from 9.36 g to 11.7 g and the addition of ammonium paramolybdate was omitted.

The composition of this catalyst (G) in atomic ratio exclusive of oxygen was as follows:

$$V_1 Cs_{0.3} Sb_{0.2} B_{0.1}$$

Thereafter, this catalyst (G) was subjected to the same reaction as in Example 1, except that the reaction temperature was changed to 430° C. The results are shown in Table 1.

It is found from the results of Table 1 that the catalyst (G) containing no molybdenum was notably deficient in selectivity and was also deficient in yield.

TABLE 1

| (No. of catalyst) | Composition catalyst (atomic ratio) | | | | Reaction temperature | Conversion (mol %) *1 | Selectivity (mol %) *2 | Per-pass yield (mol %) *3 |
|---|---|---|---|---|---|---|---|---|
| | V | Mo | X component | Y component | | | | |
| Example 1 (A) | 0.8 | 0.2 | Cs (0.3) K (0.1) | — | 450 | 79.5 | 67.8 | 53.9 |
| Example 2 (B) | 0.8 | 0.2 | Cs (0.3) | Sb (0.2) B (0.1) | 435 | 82.7 | 72.4 | 59.9 |
| Example 3 (C) | 0.8 | 0.2 | Cs (0.3) K (0.1) | P (0.3) Ag (0.1) | 425 | 79.9 | 75.6 | 60.4 |
| Example 4 | 0.75 | 0.25 | Rb (0.3) | Cu (0.2) | 430 | 80.4 | 71.8 | 57.7 |

TABLE 1-continued

| (No. of catalyst) | Composition catalyst (atomic ratio) | | | | Reaction temperature | Conversion (mol %) *1 | Selectivity (mol %) *2 | Per-pass yield (mol %) *3 |
|---|---|---|---|---|---|---|---|---|
| | V | Mo | X component | Y component | | | | |
| (D) | | | K (0.1) | Te (0.1) | | | | |
| Example 5 (E) | 0.7 | 0.3 | Tl (0.3) | P (0.2) Ba (0.1) | 430 | 80.8 | 70.4 | 56.9 |
| Example 6 (F) | 0.9 | 0.1 | Cs (0.3) | Ag (0.2) Pb (0.1) | 425 | 80.2 | 72.0 | 57.7 |
| Control 1 (G) | 1 | — | Cs (0.3) | Sb (0.2) B (0.1) | 430 | 81.9 | 59.9 | 49.1 |

*1 Conversion of p-tert-butyltoluene
*2 Selectivity of p-tert-butylbenzaldehyde
*3 Per-pass yield of p-tert-butylbenzaldehyde

EXAMPLE 7

A homogeneous solution was prepared by adding 9.36 g of ammonium metavanadate and 3.33 g of ammonium paramolybdate and further adding 14.0 g of oxalic acid to 200 ml of hot water. To this homogeneous solution, an aqueous solution of 7.80 g of cesium nitrate in 50 ml of water was added. The mixture consequently obtained was stirred at 70° C. for about one hour, then admixed with 6.82 g of the same diatomaceous earth as used in Example 1, and subsequently concentrated by heating. The resultant concentrate was dried first at 120° C. for two hours and then at 220° C. for 16 hours and subsequently calcined at 600° C. for six hours to obtain a catalyst (H).

The composition of this catalyst (H) in atomic ratio exclusive of oxygen was as follows:

$V_{0.8} Mo_{0.2} Cs_{0.4}$

P-methoxybenzaldehyde was obtained by following the procedure of Example 1, except that the catalyst (H) was used in the place of the catalyst (A), a mixed gas containing 1% by volume of p-methoxytoluene and 99% by volume of air was used instead as the feed gas, the space velocity was changed from 5,000 hr$^{-1}$ to 3,000 hr$^{-1}$, and the reaction temperature was changed from 450° C. to 440° C. The results are shown in Table 2.

EXAMPLE 8

A catalyst (I) was prepared by following the procedure of Example 7, except that 4.37 g of antimony trioxide was additionally used after the addition of the aqueous solution of cesium nitrate.

The composition of this catalyst (I) in atomic ratio exclusive of oxygen was as follows:

$V_{0.8} Mo_{0.2} Cs_{0.4} Sb_{0.3}$

Thereafter, the catalyst (I) was subjected to the same reaction as in Example 7, except that the reaction temperature was changed to 430° C. The results are shown in Table 2.

EXAMPLE 9

A catalyst (J) was prepared by following the procedure of Example 7, except that an aqueous solution of 1.70 g of silver nitrate in 10 ml of water was added and 3.46 g of 85% phosphoric acid was further added after the addition of the aqueous solution of cesium nitrate.

The composition of this catalyst (J) in atomic ratio exclusive of oxygen was as follows:

$V_{0.8} Mo_{0.2} Cs_{0.4} P_{0.3} Ag_{0.1}$

Thereafter, the catalyst (J) was subjected to the same reaction as in Example 7, except that the reaction temperature was changed to 430° C. The results are shown in Table 2.

EXAMPLE 10

A homogeneous solution was prepared by adding 8.78 g of ammonium metavanadate and 4.42 g of ammonium paramolybdate and further adding 13.2 g of oxalic acid to 200 ml of water. To this homogeneous solution, aqueous solutions of 10.65 g of thallium (I) nitrate in 50 ml of water, 2.95 g of rubidium nitrate in 10 ml of water, and 2.42 g of copper (II) nitrate in 10 ml of water were added. The mixture consequently obtained was stirred at 70° C. for about one hour, then admixed with 6.82 g of the same diatomaceous earth as used in Example 1, and subsequently concentrated by heating. The resultant concentrate was dried first at 120° C. for two hours and then at 220° C. for 16 hours and subsequently calcined at 600° C. for six hours to obtain a catalyst (K).

The composition of this catalyst (K) in atomic ratio exclusive of oxygen was as follows:

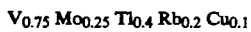

$V_{0.75} Mo_{0.25} Tl_{0.4} Rb_{0.2} Cu_{0.1}$

Thereafter, the catalyst (K) was subjected to the same reaction as in Example 7, except that the reaction temperature was changed to 430° C. The results are shown in Table 2.

Control 2

A catalyst (L) was prepared by following the procedure of Example 7, except that the amount of ammonium metavanadate to be used was changed to 11.7 g and the addition of ammonium paramolybdate was omitted.

The composition of this catalyst (L) in atomic ratio exclusive of oxygen was as follows:

$V_1 Cs_{0.4}$

Thereafter, this catalyst (L) was subjected to the same reaction as in Example 7, except that the reaction temperature was changed to 400° C. The results are shown in Table 2.

EXAMPLE 11

3,4-Dimethoxybenzaldehyde was obtained by following the procedure of Example 9, except that 3,4-dimethoxytoluene was used as a raw material in the place of p-methoxytoluene. The results are shown in Table 3.

EXAMPLE 12

3,4,5-Trimethoxybenzaldehyde was obtained by following the procedure of Example 9, except that 3,4,5-trimethoxytoluene was used as a raw material in the place of p-methoxytoluene. The results are shown in Table 4.

for 16 hours and subsequently calcined at 600° C. for six hours to obtain a catalyst (M) aimed at.

The composition of this catalytically active substance in atomic ratio exclusive of oxygen was as follows:

$V_1 Mo_{0.2} Cs_{0.3} P_{0.3} Cu_{0.1}$ $(V_{0.83} Mo_{0.17} Cs_{0.25} P_{0.25} Cu_{0.083})$

TABLE 2

| (No. of catalyst) | Composition catalyst (atomic ratio) | | | | Reaction temperature | Conversion (mol %) *1 | Selectivity (mol %) *2 | Per-pass yield (mol %) *3 |
| --- | --- | --- | --- | --- | --- | --- | --- | --- |
| | V | Mo | X component | Y component | | | | |
| Example 7 (H) | 0.8 | 0.2 | Cs (0.4) | — | 440 | 95.8 | 76.3 | 73.9 |
| Example 8 (I) | 0.8 | 0.2 | Cs (0.4) | Sb (0.3) | 430 | 94.0 | 82.4 | 77.5 |
| Example 9 (J) | 0.8 | 0.2 | Cs (0.4) | Ag (0.1) P (0.3) | 430 | 95.5 | 86.1 | 82.2 |
| Example 10 (K) | 0.75 | 0.25 | Tl (0.4) Rb (0.2) | Cu (0.1) | 430 | 94.5 | 83.2 | 78.6 |
| Control 2 (L) | 1 | — | Cs (0.4) | — | 400 | 95.1 | 72.5 | 68.9 |

*1 Conversion of p-methoxytoluene
*2 Selectivity of p-methoxybenzaldehyde
*3 Per-pass yield of p-methoxybenzaldehyde

TABLE 3

| (No. of catalyst) | Composition catalyst (atomic ratio) | | | | Reaction temperature | Conversion (mol %) *1 | Selectivity (mol %) *2 | Per-pass yield (mol %) *3 |
| --- | --- | --- | --- | --- | --- | --- | --- | --- |
| | V | Mo | X component | Y component | | | | |
| Example 11 (J) | 0.8 | 0.2 | Cs (0.4) | Ag (0.1) P (0.3) | 430 | 96.8 | 74.3 | 71.9 |

*1 Conversion of 3,4-dimethoxytoluene
*2 Selectivity of 3,4-dimethoxybenzaldehyde
*3 Per-pass yield of 3,4-dimethoxybenzaldehyde

TABLE 4

| (No. of catalyst) | Composition catalyst (atomic ratio) | | | | Reaction temperature | Conversion (mol %) *1 | Selectivity (mol %) *2 | Per-pass yield (mol %) *3 |
| --- | --- | --- | --- | --- | --- | --- | --- | --- |
| | V | Mo | X component | Y component | | | | |
| Example 12 (J) | 0.8 | 0.2 | Cs (0.4) | Ag (0.1) P (0.3) | 430 | 98.2 | 71.4 | 70.1 |

*1 Conversion of 3,4,5-trimethoxytoluene
*2 Selectivity of 3,4,5-trimethoxybenzaldehyde
*3 Per-pass yield of 3,4,5-trimethoxybenzaldehyde

EXAMPLE 13

A homogeneous solution was prepared by adding 3.51 g of ammonium metavanadate was added to 10 ml of water, heating the resultant mixture at 70° C., and further adding 8.01 g of citric acid to the hot mixture. A homogeneous impregnating solution was prepared by adding 1.75 g of cesium nitrate, 1.00 g of ammonium paramolybdate, 1.04 g of 85% phosphoric acid, and 0.72 g of copper (II) nitrate to the homogeneous solution. A self-sintered carrier of silicon carbide possessing (silicon carbide content: not less than 98%) apparent porosity of 45% and specific surface area of 0.1 m²/g was pulverized to 9 to 20 mesh. A portion, 50 g, of the pulverized carrier was placed in an evaporation dish. On a hot water bath, the pulverized carrier in the dish was stirred and the aforementioned impregnating solution was wholly added thereto and left impregnating the carrier. The carrier impregnated with the impregnating solution was dried at 120° C. for two hours and then at 220° C.

The amount of the substance thus deposited on the carrier was 11.5% by weight based on the weight of the carrier.

A U-shaped reaction tube of stainless steel having an inside diameter of 10 mm was packed with 15 ml of the catalyst mentioned above. A mixed gas containing 1.0% by volume of p-tert-butyltoluene and 99.0% by volume of air was introduced into the reaction tube and left reacting therein at a space velocity of 3,000 hr$^{-1}$ (STP basis) and a reaction temperature of 430° C. to produce p-tert-butylbenzaldehyde. The results are shown in Table 5.

EXAMPLE 14

A catalyst (N) was prepared by following the procedure of Example 13, except that 5.59 g of malic acid instead of citric acid, 0.30 g of potassium nitrate was added after adding cesium nitrate, 25 g of ammonium paramolybdate instead of 100 g and 85% phosphoric acid and copper nitrate were not added. The composition of this catalytically active substance in atomic ratio exclusive of oxygen was as follows:

$$V_{0.80} Mo_{0.20} Cs_{0.24} K_{0.08}$$

and a deposit amount of the composition was 10.4% by weight based on the weight of the carrier.

Thereafter, the catalyst (N) was subjected to the same reaction as in Example 13, except that the reaction temperature was changed to 450° C. The results are shown in Table 5.

cally active substance in atomic ratio exclusive of oxygen was as follows:

$$V_1 Cs_{0.3} K_{0.1}$$

and a deposit amount of the composition was 8.3% by weight based on the weight of the carrier.

Thereafter, the catalyst (Q) was subjected to the same reaction as in Example 14, except that the reaction temperature was changed to 455° C. The results are shown in Table 5.

TABLE 5

| (No. of catalyst) | Composition catalyst (atomic ratio) | | | | Inactive Carrier | Oxyacid | Reaction temperature | Conversion (mol %) *1 | Selectivity (mol %) *2 | Per-pass yield (mol %) *3 |
|---|---|---|---|---|---|---|---|---|---|---|
| | V | Mo | X component | Y component | | | | | | |
| Example 13 (M) | 0.83 | 0.17 | Cs (0.25) | P (0.25) Cu (0.083) | SiC | citric acid | 455 | 79.8 | 82.3 | 65.7 |
| Example 14 (N) | 0.80 | 0.20 | Cs (0.24) K (0.08) | — | SiC | malic acid | 450 | 77.3 | 76.8 | 59.4 |
| Example 15 (O) | 0.77 | 0.23 | Tl (0.23) | B (0.077) Te (0.077) Ca (0.077) | SiC | citric acid | 435 | 80.1 | 80.2 | 64.2 |
| Example 16 (P) | 0.83 | 0.17 | Rb (0.25) K (0.083) | Sb (0.083) Ag (0.17) | SiC | citric acid | 430 | 79.7 | 79.3 | 63.2 |
| Control 3 (Q) | 1 | 0 | Cs (0.30) K (0.10) | — | SiC | malic acid | 455 | 78.6 | 71.5 | 56.2 |

*1 Conversion of p-tert-butyl toluene
*2 Selectivity of p-tert-butylbenzaldehyde
*3 Per-pass yield of p-tert-butylbenzaldehyde

EXAMPLE 15

A catalyst (O) was prepared by following the procedure of Example 13, except that 2.40 g of thallium (I) nitrate instead of cesium nitrate, 1.50 g of ammonium paramolybdate instead of 100 g, 0.37 g of boric acid, 0.69 g of telluric acid and 0.49 g of calcium nitrate instead of nitrate were used. The composition of this catalytically active substance in atomic ratio exclusive of oxygen was as follows:

$$V_{0.77} Mo_{0.23} Tl_{0.23} B_{0.077} Te_{0.077} Ca_{0.077}$$

and a deposit amount of the composition was 13.2% by weight based on the weight of the carrier. Thereafter, the catalyst (O) was subjected to the same reaction as in Example 13, except that the reaction temperature was changed to 450° C. The results are shown in Table 5.

EXAMPLE 16

A catalyst (P) was prepared by following the procedure of Example 13, except that 1.33 g of rubidium nitrate and 1.00 g of potassium tartarate ammonyl instead of cesium nitrate and 1.02 g of silver nitrate instead of copper (II) nitrate were used. The composition of this catalytical active substance in atomic ratio exclusive of oxygen was as follows:

$$V_{0.83} Mo_{0.17} Rb_{0.25} K_{0.083} Sb_{0.083} Ag_{0.17}$$

and a deposit amount of composition was 11.0% by weight based on the weight of the carrier.

Thereafter, the catalyst (P) was subjected to the same reaction as in Example 13, except that the reaction temperature was changed to 450° C. The results are shown in Table 5.

A catalyst (Q) was prepared by following the procedure of Example 14, except that ammonium paramolybdate was not added. The composition of this catalyti-

EXAMPLE 17

A homogeneous solution was prepared by adding 3.51 g of ammonium metavanadate was added to 10 ml of water, heating the resultant mixture at 70° C., and further adding 8.01 g of citric acid to the hot mixture. A homogeneous impregnating solution was prepared by adding 2.34 g of cesium nitrate, 1.50 g of ammonium paramolybdate, and 0.72 g of copper (II) nitrate to the homogeneous solution. A self-sintered carrier of silicon carbide possessing (silicon carbide content: not less than 98%) apparent porosity of 45% and specific surface area of 0.1 m²/g was pulverized to 9 to 20 mesh. A portion, 50 g, of the pulverized carrier was placed in an evaporation dish. On a hot water bath, the pulverized carrier in the dish was stirred and the aforementioned impregnating solution was wholly added thereto and left impregnating the carrier. The carrier impregnated with the impregnating solution was dried at 120° C. for two hours and then at 220° C. for 16 hours and subsequently calcined at 600° C. for six hours to obtain a catalyst (R) aimed at.

The composition of this catalytically active substance in atomic ratio exclusive of oxygen was as follows:

$$V_{0.77} Mo_{0.23} Cs_{0.31} Cu_{0.077}$$

The amount of the substance thus deposited on the carrier was 11.9% by weight based on the weight of the carrier.

Thereafter, the catalyst (R) was subjected to the same reaction as Example 13 except that paramethoxy toluene was used as a starting raw gas instead of p-tert-butyltoluene and the reaction temperature was changed from 455° C. to 410° C. to obtain p-methocybenzaldehyde. The results are shown in Table 6.

Control 4

A catalyst (S) was prepared by the following the procedure of Example 17, except that ammonium paramolybdate was not added. The composition of this catalytically active substance in atomic ratio exclusive of oxygen was as follows:

$V_1 Cs_{0.4} Cu_{0.1}$

The amount of the substance thus deposited on the carrier was 9.3% by weight based on the weight of the carrier.

Thereafter, the catalyst (R) was subjected to the reaction as in Example 17, except that the reaction temperature was changed to 420° C. The results are shown in Table 6.

TABLE 6

| (No. of catalyst) | Composition catalyst (atomic ratio) | | | | Inactive Carrier | Oxyacid | Reaction temperature | Conversion (mol %) *1 | Selectivity (mol %) *2 | Per-pass yield (mol %) *3 |
|---|---|---|---|---|---|---|---|---|---|---|
| | V | Mo | X component | Y component | | | | | | |
| Example 17 (R) | 0.77 | 0.23 | Cs (0.31) | Cu (0.077) | SiC | citric acid | 410 | 94.5 | 85.0 | 80.3 |
| Control 4 (S) | 1 | 0 | Cs (0.40) | Cu (0.10) | SiC | citric acid | 420 | 92.8 | 83.9 | 77.9 |

*1 Conversion of p-methoxytoluene
*2 Selectivity of p-methoxybenzaldehyde
*3 Per-pass yield of p-methoxybenzaldehyde

We claim:

1. A catalyst for the production of a substituted benzaldehyde represented by the general formula I:

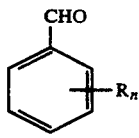

(I)

wherein R is tert-butyl group, methoxy group, phenoxy group, isopropyl group, or hydroxyl group and n is an integer in the range of from 1 to 3, by catalytic vapor-phase oxidation of a substituted toluene represented by the general formula II:

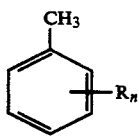

(II)

wherein R and n are the same meanings as defined above, which catalyst has a catalytically active substance an oxide represented by the general formula III

(III)

wherein V, Mo, and O are respectively vanadium, molybdenum, and oxygen, X is at least one element selected from the group consisting of potassium, rubidium, cesium, and thallium, Y is at least one element selected from the group consisting of niobium, tantalum, phosphorus, antimony, bismuth, tellurium, tin, lead, boron, copper, and silver, and a, b, c, d, and e indicate the atomic ratios of relevant elements such that where $a+b=1$, then $b=0.05$ to 0.4, $c=0.1$ to 1, $d=0$ to 1, and $e=$ the value determined by the state of oxidation of other elements.

2. A catalyst according to claim 1, which is formed by molding a catalytically active component.

3. A catalyst according to claim 1, wherein said catalytically active component is mixed with powdered inactive carrier and then molded.

4. A catalyst according to claim 1, which is formed by depositing an amount of a catalytically active component on a porous inactive carrier wherein the amount of said catalytically active substance deposited on said porous inactive carrier is in the range of 3 to 20% by weight based on the weight of the said porous inactive carrier, and said porous inactive carrier has apparent porosity in the range of from 20 to 60% and specific surface area in the range of from 0.01 to 1 $m^2$-g.

5. A catalyst according to claim 3, wherein the amount of said powdered inactive carrier is in the range of from 10 to 80% by weight, based on the weight of said catalyst in a finished form.

6. A method for the production of a catalyst to be used in the preparation a substituted benzaldehyde represented by the general formula I:

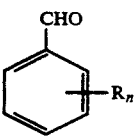

(I)

wherein R is tert-butyl group, methoxy group, phenoxy group, isopropyl group, or hydroxy group and n is an integer in the range of from 1 to 3, by catalytic vapor-phase oxidation of a substituted toluene represented by the general formula II:

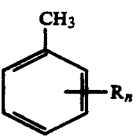

(II)

wherein R and n have the same meanings as defined above, which method comprises mixing a powdered inactive carrier with the starting raw materials for an oxide represented by the general formula III:

(III)

wherein V, Mo, and O are respectively vanadium, molybdenum, and oxygen, X is at least one element selected from the group consisting of potassium, rubidium, cesium, and thallium, Y is at least one element selected from the group consisting of niobium, tantalum, phosphorus, antimony, bismuth, tellurium, tin, lead, boron, copper, and silver, and a, b, c, d, and e indicate the atomic ratios of relevant elements such that where a+b=1, then b=0.05 to 0.4, c =0.1 to 1, d=0 to 1, and e=the value determined by the state of oxidation of other elements, molding the resultant mixture, drying the molded particulates and calcining the dried particulates.

7. A method according to claim 6 wherein the amount of powdered inactive carrier mixed with said starting raw materials for an oxide represented by the general formula III is in the range of from 10 to 80% by weight, based on the amount of said catalyst in a finished form.

8. A method for the production of a catalyst to be used in the preparation of a substituted benzaldehyde which method comprises depositing on a porous inactive carrier the starting raw materials for a catalytically active oxide represented by the general formula III:

$$V_a Mo_b X_c Y_d O_e \qquad (III)$$

wherein V, Mo, and O are respectively vanadium, molybdenum, and oxygen, X is at least one element selected from the group consisting of potassium, rubidium, cesium, and thallium, Y is at least one element selected from the group consisting of niobium, tantalum, phosphorus, antimony, bismuth, tellurium, tin, lead, boron, copper, and silver, and a, b, c, d, and e indicate the atomic ratios of relevant elements such that where a+b=1, then b=0.05 to 0.4, c=0.1 to 1, d=0 to 1, and e=the value determined by the state of oxidation of other elements, drying the deposited carrier and calcining the dried carrier, wherein the amount of said catalytically active oxide is in the range of from 3 to 20% by weight, based on the weight of said porous inactive carrier, and said porous inactive carrier has apparent porosity in the range of frm 20 to 60% and specific surface area in the range of 0.1 to 1 m²/g.

9. A method according to claim 8, wherein said starting raw materials for said composite oxide represented by the general formula III are mixed with an oxyacid and then deposited on said porous inactive carrier.

10. A method according to claim 9, wherein said oxy-acid is at least one member selected from the group consisting of lactic acid, malic acid, tartaric acid, and citric acid.

* * * * *